United States Patent
Cok et al.

(10) Patent No.: US 9,434,146 B2
(45) Date of Patent: *Sep. 6, 2016

(54) USING IMPRINTED PARTICLE STRUCTURE

(71) Applicant: Eastman Kodak Company, Rochester, NY (US)

(72) Inventors: Ronald Steven Cok, Rochester, NY (US); Mitchell Stewart Burberry, Webster, NY (US)

(73) Assignee: EASTMAN KODAK COMPANY, Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/526,691

(22) Filed: Oct. 29, 2014

(65) Prior Publication Data

US 2016/0121594 A1   May 5, 2016

(51) Int. Cl.
| | |
|---|---|
| *B32B 37/14* | (2006.01) |
| *B32B 37/16* | (2006.01) |
| *B32B 37/06* | (2006.01) |
| *B32B 38/10* | (2006.01) |
| *C09K 13/00* | (2006.01) |
| *B32B 38/16* | (2006.01) |
| *G03F 7/00* | (2006.01) |
| *A01N 25/10* | (2006.01) |

(52) U.S. Cl.
CPC .............. *B32B 37/14* (2013.01); *B32B 37/06* (2013.01); *B32B 38/10* (2013.01); *B32B 38/162* (2013.01); *C09K 13/00* (2013.01); *A01N 25/10* (2013.01); *B32B 2305/72* (2013.01); *G03F 7/0002* (2013.01)

(58) Field of Classification Search
None
See application file for complete search history.

(56) References Cited

U.S. PATENT DOCUMENTS

| | | | |
|---|---|---|---|
| 5,662,991 A | 9/1997 | Smolik et al. | |
| 5,980,620 A | 11/1999 | Brodie et al. | |
| 6,437,021 B1 * | 8/2002 | Wettling | ................. A01N 25/10 424/405 |
| 6,955,845 B1 * | 10/2005 | Poole | ....................... B23B 3/02 296/39.3 |
| 7,143,709 B2 * | 12/2006 | Brennan | ................. B08B 17/06 114/222 |
| 7,579,396 B2 | 8/2009 | Blanton et al. | |
| 2006/0195176 A1 | 8/2006 | Bates et al. | |
| 2006/0248767 A1 * | 11/2006 | Hofer | ...................... A61L 15/46 40/633 |
| 2008/0242794 A1 | 10/2008 | Sandford et al. | |
| 2009/0291147 A1 | 11/2009 | Sandford et al. | |
| 2010/0034900 A1 * | 2/2010 | Temchenko | ........... A01N 25/10 424/618 |
| 2010/0093851 A1 | 4/2010 | Blanton et al. | |
| 2010/0160486 A1 | 6/2010 | Blanton et al. | |
| 2010/0167181 A1 | 7/2010 | Kim | |
| 2010/0263793 A1 | 10/2010 | Ylitalo et al. | |

(Continued)

FOREIGN PATENT DOCUMENTS

| | | |
|---|---|---|
| CN | 102063951 | 5/2011 |
| JP | 09078789 A * | 3/1997 |
| JP | 09123380 A * | 5/1997 |

*Primary Examiner* — Anita Alanko
(74) *Attorney, Agent, or Firm* — Raymond L. Owens; William R. Zimmerli

(57) ABSTRACT

A method of using a multi-layer biocidal structure includes providing a multi-layer biocidal structure having a support and a structured bi-layer on or over the support. The structured bi-layer includes a first cured layer on or over the support and a second layer in a spatial relationship to the first cured layer on a side of the first cured layer opposite the support. The structured bi-layer has at least one depth greater than the thickness of the second layer and multiple biocidal particles located only in the second layer. The multi-layer biocidal structure is located on a surface.

19 Claims, 21 Drawing Sheets

(56) References Cited

U.S. PATENT DOCUMENTS

| | | | |
|---|---|---|---|
| 2011/0217544 A1* | 9/2011 | Young | B29C 37/0032 428/327 |
| 2012/0164433 A1 | 6/2012 | Advincula | |
| 2013/0056244 A1* | 3/2013 | Srinivas | G06F 3/041 174/250 |
| 2014/0170298 A1 | 6/2014 | Terry et al. | |
| 2014/0193612 A1 | 7/2014 | Yu et al. | |

* cited by examiner

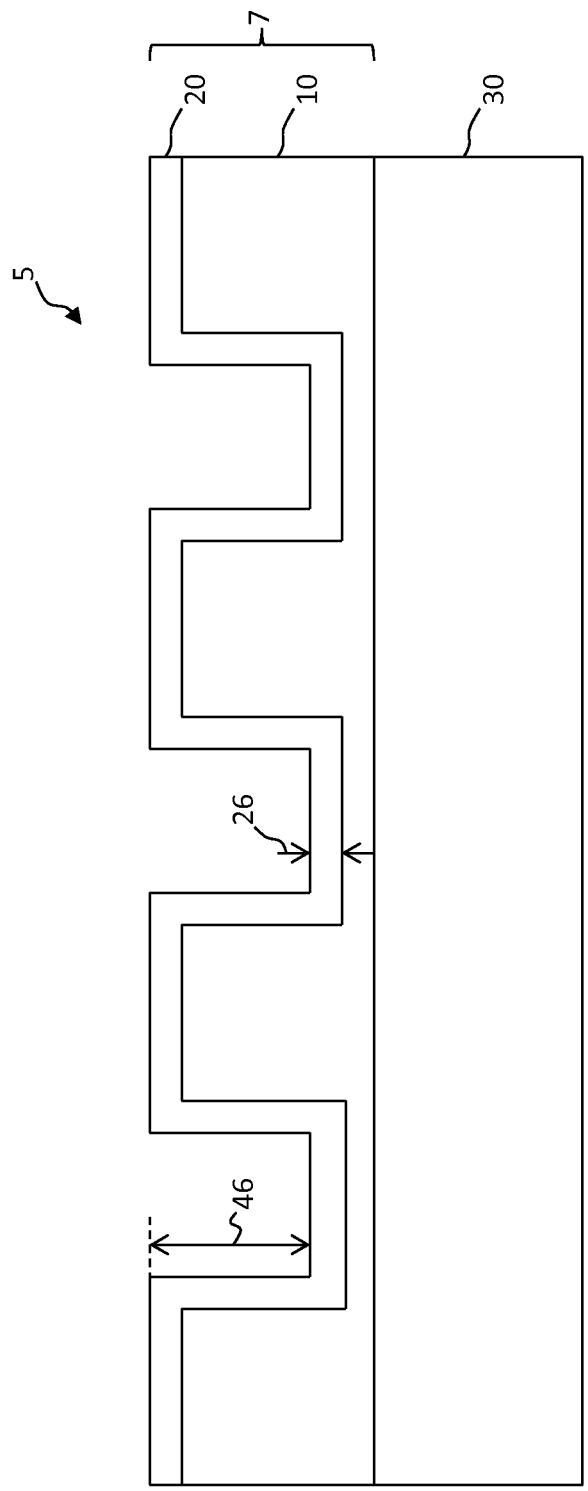

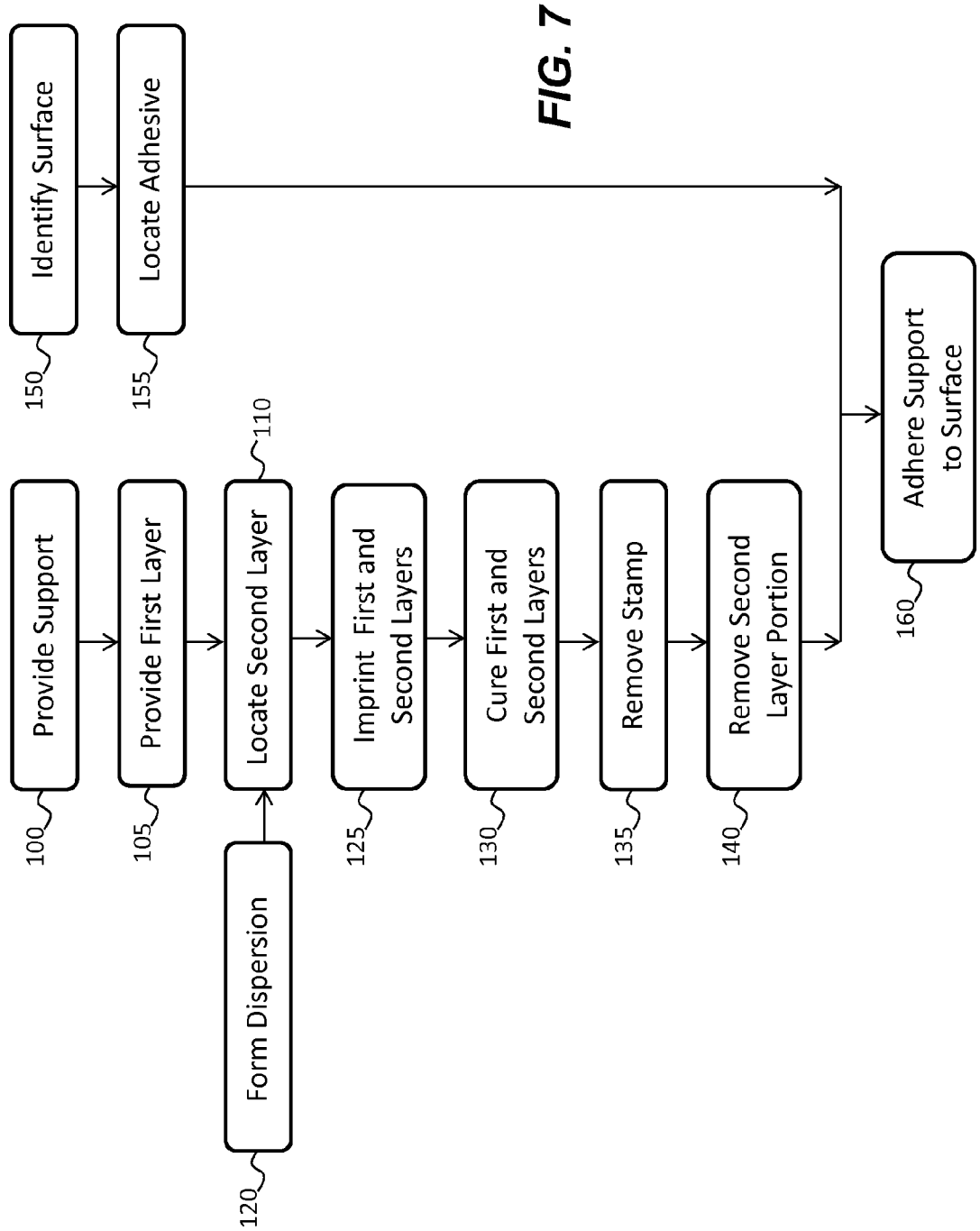

USING IMPRINTED PARTICLE STRUCTURE

CROSS REFERENCE TO RELATED APPLICATIONS

Reference is made to commonly-assigned co-pending U.S. patent application Ser. No. 14/526,595, filed Oct. 29, 2014, entitled Imprinted Multi-layer Structure, by Cok et al, to commonly-assigned U.S. patent application Ser. No. 14/526,603 (now U.S. Pat. No. 9,186,698), filed Oct. 29, 2014, entitled Making Imprinted Multi-layer Structure, by Cok et al, to commonly-assigned co-pending U.S. patent application Ser. No. 14/526,611, filed Oct. 29, 2014, entitled Imprinted Multi-layer Biocidal Particle Structure, by Cok et al, to commonly-assigned co-pending U.S. patent application Ser. No. 14/526,619, filed Oct. 29, 2014, entitled Making Imprinted Multi-layer Biocidal Particle Structure, by Cok et al, to commonly-assigned co-pending U.S. patent application Ser. No. 14/526,640, filed Oct. 29, 2014, entitled Using Imprinted Multi-layer Biocidal Particle Structure, by Cok et al, to commonly-assigned co-pending U.S. patent application Ser. No. 14/526,646, filed Oct. 29, 2014, entitled Imprinted Particle Structure, by Cok et al, to commonly-assigned co-pending U.S. patent application Ser. No. 14/526,666, filed Oct. 29, 2014, entitled Making Imprinted Particle Structure, by Cok et al, and to commonly-assigned co-pending U.S. patent application Ser. No. 14/519,489, filed Oct. 21, 2014, entitled Using Colored Biocidal Multi-Layer Structure, by Scheible et al, the disclosures of which are incorporated herein.

FIELD OF THE INVENTION

The present invention relates to biocidal layers having antimicrobial efficacy on a surface.

BACKGROUND OF THE INVENTION

Widespread attention has been focused in recent years on the consequences of bacterial and fungal contamination contracted by contact with common surfaces and objects. Some noteworthy examples include the sometimes fatal outcome from food poisoning due to the presence of particular strains of *Escherichia coli* in undercooked beef; *Salmonella* contamination in undercooked and unwashed poultry food products; as well as illnesses and skin irritations due to *Staphylococcus aureus* and other micro-organisms. Anthrax is an acute infectious disease caused by the spore-forming bacterium *bacillus anthracis*. Allergic reactions to molds and yeasts are a major concern to many consumers and insurance companies alike. In addition, significant fear has arisen in regard to the development of antibiotic-resistant strains of bacteria, such as methicillin-resistant *Staphylococcus aureus* (MRSA) and vancomycin-resistant *Enterococcus* (VRE). The U.S. Centers for Disease Control and Prevention estimates that 10% of patients contract additional diseases during their hospital stay and that the total deaths resulting from these nosocomially-contracted illnesses exceeds those suffered from vehicular traffic accidents and homicides. In response to these concerns, manufacturers have begun incorporating antimicrobial agents into materials used to produce objects for commercial, institutional, residential, and personal use.

Noble metal ions such as silver and gold ions are known for their antimicrobial properties and have been used in medical care for many years to prevent and treat infection. In recent years, this technology has been applied to consumer products to prevent the transmission of infectious disease and to kill harmful bacteria such as *Staphylococcus aureus* and *Salmonella*. In common practice, noble metals, metal ions, metal salts, or compounds containing metal ions having antimicrobial properties can be applied to surfaces to impart an antimicrobial property to the surface. If, or when, the surface is inoculated with harmful microbes, the antimicrobial metal ions or metal complexes, if present in effective concentrations, will slow or even prevent altogether the growth of those microbes. Recently, silver sulfate, $Ag_2SO_4$, described in U.S. Pat. No. 7,579,396, U.S. Patent Application Publication 2008/0242794, U.S. Patent Application Publication 2009/0291147, U.S. Patent Application Publication 2010/0093851, and U.S. Patent Application Publication 2010/0160486 has been shown to provide efficacious antimicrobial protection in polymer composites. The United States Environmental Protection Agency (EPA) evaluated silver sulfate as a biocide and registered its use as part of EPA Reg. No, 59441-8 EPA EST. NO. 59441-NY-001. In granting that registration, the EPA determined that silver sulfate was safe and effective in providing antibacterial and antifungal protection.

Antimicrobial activity is not limited to noble metals but is also observed in other metals such as copper and organic materials such as triclosan, and some polymeric materials.

It is important that the antimicrobial active element, molecule, or compound be present on the surface of the article at a concentration sufficient to inhibit microbial growth. This concentration, for a particular antimicrobial agent and bacterium, is often referred to as the minimum inhibitory concentration (MIC). It is also important that the antimicrobial agent be present on the surface of the article at a concentration significantly below that which can be harmful to the user of the article. This prevents harmful side effects of the article and decreases the risk to the user, while providing the benefit of reducing microbial contamination. There is a problem in that the rate of release of antimicrobial ions from antimicrobial films can be too facile, such that the antimicrobial article can quickly be depleted of antimicrobial active materials and become inert or non-functional. Depletion results from rapid diffusion of the active materials into the biological environment with which they are in contact, for example, water soluble biocides exposed to aqueous or humid environments. It is desirable that the rate of release of the antimicrobial ions or molecules be controlled such that the concentration of antimicrobials remains above the MIC. The concentration should remain there over the duration of use of the antimicrobial article. The desired rate of exchange of the antimicrobial can depend upon a number of factors including the identity of the antimicrobial metal ion, the specific microbe to be targeted, and the intended use and duration of use of the antimicrobial article.

Antimicrobial coatings are known in the prior art, for example as described in U.S. Patent Application Publication No. 2010/0034900. This disclosure teaches a method of coating a substrate with biocide particles dispersed into a coating so that the particles are in contact with the environment. Non-planar coatings are also known to provide surface topographies for non-toxic bio-adhesion control, for example as disclosed in U.S. Pat. No. 7,143,709.

Imprinting methods useful for forming surface topographies are taught in CN102063951. As discussed in CN102063951, a pattern of micro-channels are formed in a substrate using an embossing technique. Embossing methods are generally known in the prior art and typically include coating a curable liquid, such as a polymer, onto a rigid substrate. A pattern of micro-channels is embossed (impressed or imprinted) onto the polymer layer by a master having an inverted pattern of structures formed on its surface. The polymer is then cured.

Fabrics or materials incorporating biocidal elements are known in the art and commercially available. U.S. Pat. No. 5,662,991 describes a biocidal fabric with a pattern of biocidal beads. U.S. Pat. No. 5,980,620 discloses a means of inhibiting bacterial growth on a coated substrate comprising a substantially dry powder coating containing a biocide. U.S. Pat. No. 6,437,021 teaches a water-insoluble polymeric support containing a biocide. Methods for depositing thin silver-comprising films on non-conducting substrates are taught in U.S. Patent Application Publication No. 2014/0170298.

SUMMARY OF THE INVENTION

The efficacy of antimicrobial coatings and materials depend at least in part on their structure and surface area. The cost of the coatings also depends upon the quantity of materials in the coatings. There is a need, therefore, for antimicrobial coatings with improved efficacy and reduced costs.

In accordance with the present invention, a method of using a multi-layer biocidal structure includes:

providing a multi-layer biocidal structure that includes a support and a structured bi-layer on or over the support, the structured bi-layer including a first cured layer on or over the support, a second layer in a spatial relationship to the first cured layer on a side of the first cured layer opposite the support, the structured bi-layer having at least one depth greater than the thickness of the second layer and multiple biocidal particles located only in the second layer; and locating the multi-layer biocidal structure on a surface.

The present invention provides a biocidal multi-layer structure that provides improved antimicrobial properties with thinner layers having increased surface area made in a cost-efficient process.

BRIEF DESCRIPTION OF THE DRAWINGS

The above and other features and advantages of the present invention will become more apparent when taken in conjunction with the following description and drawings wherein identical reference numerals have been used to designate identical features that are common to the figures, and wherein:

FIGS. 4A-4F are cross sections of sequential construction steps useful in a method of the present invention;

FIG. 7 is a flow diagram illustrating a method of the present invention;

The Figures are not drawn to scale since the variation in size of various elements in the Figures is too great to permit depiction to scale.

DETAILED DESCRIPTION OF THE INVENTION

The present invention provides a multi-layer structure useful in forming an antimicrobial article on a support. Multi-layer structures of the present invention provide improved antimicrobial properties with thinner layers having increased surface area made in a cost-efficient process. In useful methods of the present invention, multiple uncured coatings are formed on a support, imprinted together, and then cured together. A thin top layer can include reduced quantities of antimicrobial materials or antimicrobial particles. The imprinted layers provide a greater surface area for the antimicrobial materials and a topographical structure that inhibits the growth and reproduction of microbes. Coating and imprinting processes provide a cost-efficient manufacturing method.

Figure 1:
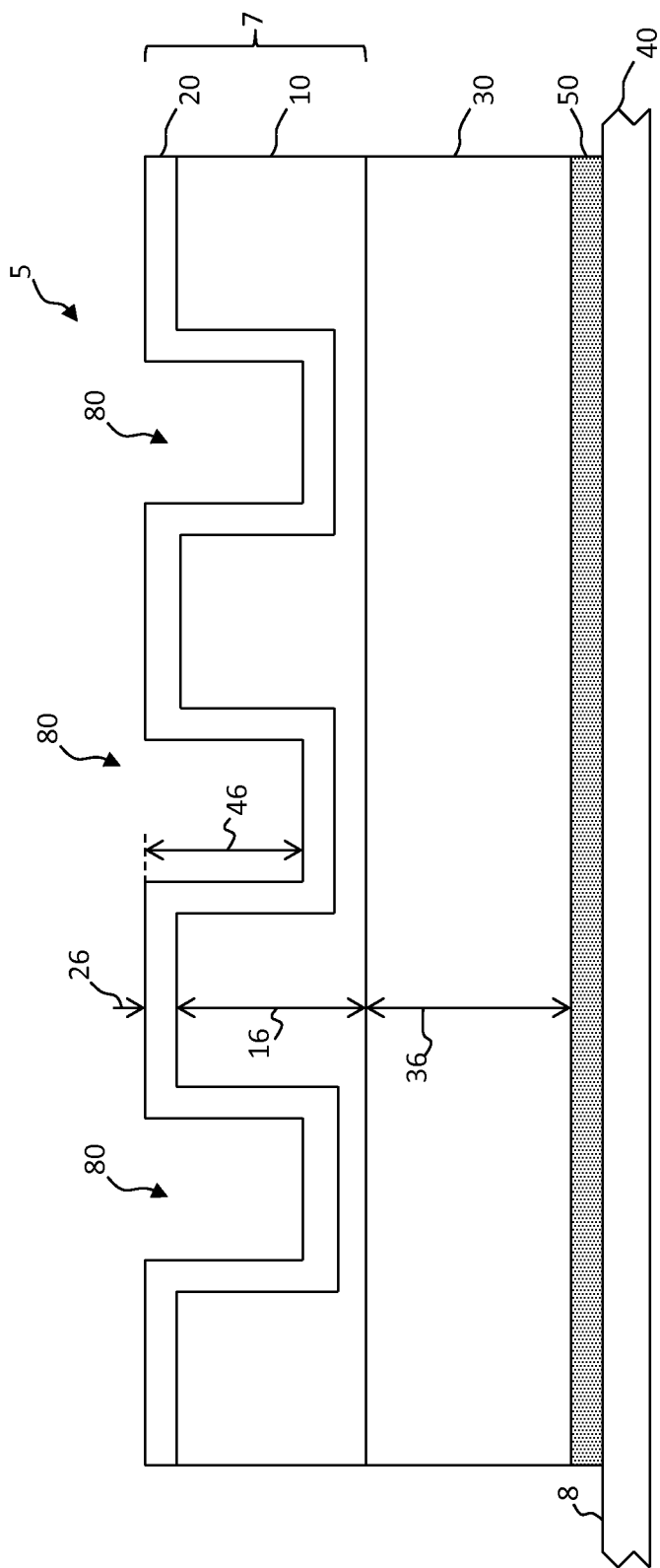
FIG. 1 is a cross section of a multi-layer structure illustrating an embodiment of the present invention.

Referring to FIG. 1, in an embodiment of the present invention, an imprinted multi-layer structure 5 includes a support 30 having a support thickness 36. A bi-layer 7 having a topographical structure is located on or over the support 30. The structured bi-layer 7 includes a first cured layer 10 including a first cross-linked material on or over the support 30 and a second cured layer 20 including a second material different from the first material on or over the first cured layer 10 on a side of the first cured layer 10 opposite the support 30. The first cured layer 10 has a first cured layer thickness 16 and the second cured layer 20 has a second-layer thickness 26. Indentations 80 are located in the first and second cured layers 10, 20 to form a topographical structure with a depth 46. The first material of the first cured layer 10 is cross-linked to the second material of the second cured layer 20 and the depth 46 of the bi-layer 7 structure is greater than the second-layer thickness 26 of the second cured layer 20. Coating or other deposition methods for forming multiple layers on a substrate are known in the art, as are imprinting methods useful for forming the indentations 80 in the first and second cured layers 10, 20.

In an embodiment, the second cured layer 20 is thinner than the first cured layer 10. As shown in FIG. 1, the first cured layer 10 has portions with the first-layer thickness 16 that are thicker than the second-layer thickness 26.

As used herein, a structured layer is a layer that is not smooth or not planar on a microscopic scale corresponding to the magnitude of the indentations 80. For example if the support 30 is planar, a structured layer formed on the support 30 according to the present invention is flat but non-planar and is not smooth. If the support 30 is not planar but is smooth, for example having a surface that is curved in one or more dimensions (such as a spherical section), a structured layer formed on the support 30 according to the present invention is also non-planar but is not smooth. Whether or not the support 30 is planar, the structured layer can include indentations 80, channels, pits, holes, extended portions, mesas or other physical elements or structures. In one embodiment, the surface is rough. The structure depth 46 of the structured bi-layer 7 is the distance from the portion of the structured bi-layer 7 furthest from the support 30 to the portion of the structured bi-layer 7 that is closest to the support 30 in a direction that is orthogonal to a surface of the support 30.

In an embodiment, the first cured layer 10 is located on or over the support 30. The support 30 is any layer that is capable of supporting the first and second cured layers 10, 20 and in different embodiments is rigid, flexible, or transparent and, for example is a substrate made of glass, plastic, paper, or vinyl or combinations of such materials or other materials. In an embodiment, the first cured layer 10 is cross linked to the second cured layer 20 to provide rigidity and improved strength for the layers.

In a useful arrangement, the support 30 is adhered, for example with an adhesive layer 50 such as a pressure-sensitive adhesive or glue such as wall-paper glue, to a surface 8 of a structure 40. The surface 8 is any surface 8, planar or non-planar that is desired to resist the growth of biologically undesirable organisms, including microbes, bacteria, or fungi. In various applications, the structure 40 is a structure such as a wall, floor, table top, door, handle, cover, device, or any structure 40 having the surface 8 likely to come into contact with a human. The imprinted multi-layer structure 5 can form a wall paper or plastic wrap for structures 40.

In an embodiment of the present invention, the second cured layer 20 includes a second material that is different from the first cross-linked material in the first cured layer 10. In another embodiment of the present invention, the second material includes a second cross-linked material that is the same as the first cross-linked material. In this embodiment, either the first cross-linked material includes a third material that is not in the second cross-linked material or the second cross-linked material includes a third material that is not in the first cross-linked material. Therefore, the first cross-linked material and second material are different or include different materials.

In one embodiment, the second cured layer 20 is electrically conductive and the first cured layer 10 is electrically insulating. Electrically conductive materials, for example polyethyldioxythiophene (PEDOT) are known in the art, as are insulating polymers or resins. In an embodiment, the second cured layer 20 is electrically conductive.

Figure 2A:
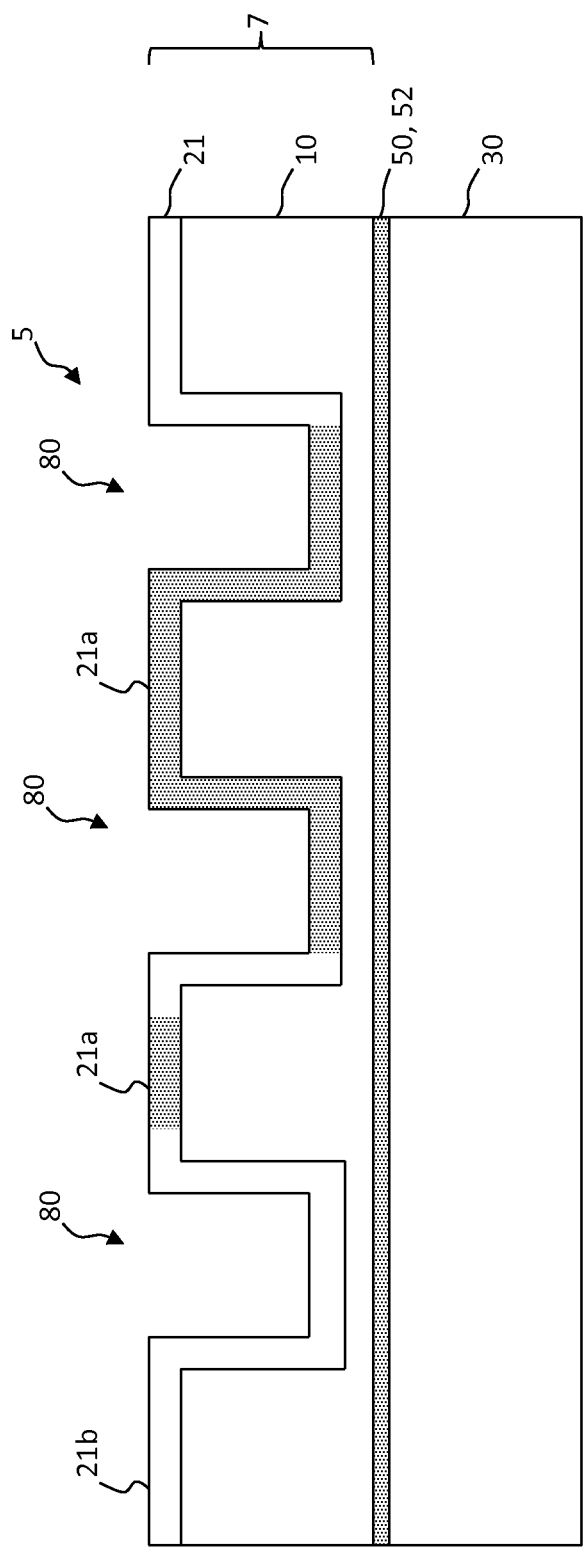
FIGS. 2A and 2B are cross sections of multi-layer structures in other embodiments of the present invention.

Referring to FIG. 2A, in another embodiment the second cured layer 20 (FIG. 1) is chemically patterned to form a patterned second cured layer 21 that has conductive portions 21a and non-conductive portions 21b. Materials and methods for pattern-wise inhibiting the electrical conductivity of PEDOT are known. By patterning such inhibiting chemicals over the extent of the second cured layer 20 (FIG. 1), the electrical conductivity of the second cured layer 20 is likewise patterned to form the patterned second cured layer 21 with conductive portions 21a and non-conductive portions 21b.

As shown in FIG. 2A in a further embodiment, a binder primer 52 is located between the first cured layer 10 and the support 30. The binder primer 52 can be an adhesive layer 50 that adheres the first cured layer 10 to the support 30. Alternatively, or in addition, the binder primer 52 can form a support surface on which the first cured layer 10 is readily coated, for example by controlling the surface energy of the support surface or the first cured layer 10. In another embodiment not shown in FIG. 1 or 2, the binder primer 52 or the adhesive 50 is located between the first cured layer 10 and the second cured layer 20 or the patterned second cured layer 21 to adhere the first cured layer 10 and the second cured layers 20 or the patterned second cured layer 21 together and enable the second cured layer 20 or the patterned second cured layer 21 to be coated over the first cured layer 10 before the first cured layer 10 and the second cured layer 20 or the patterned second cured layer 21 are imprinted to form the indentations 80 of the bi-layer 7 and the imprinted multi-layer structure 5.

Figure 2B:
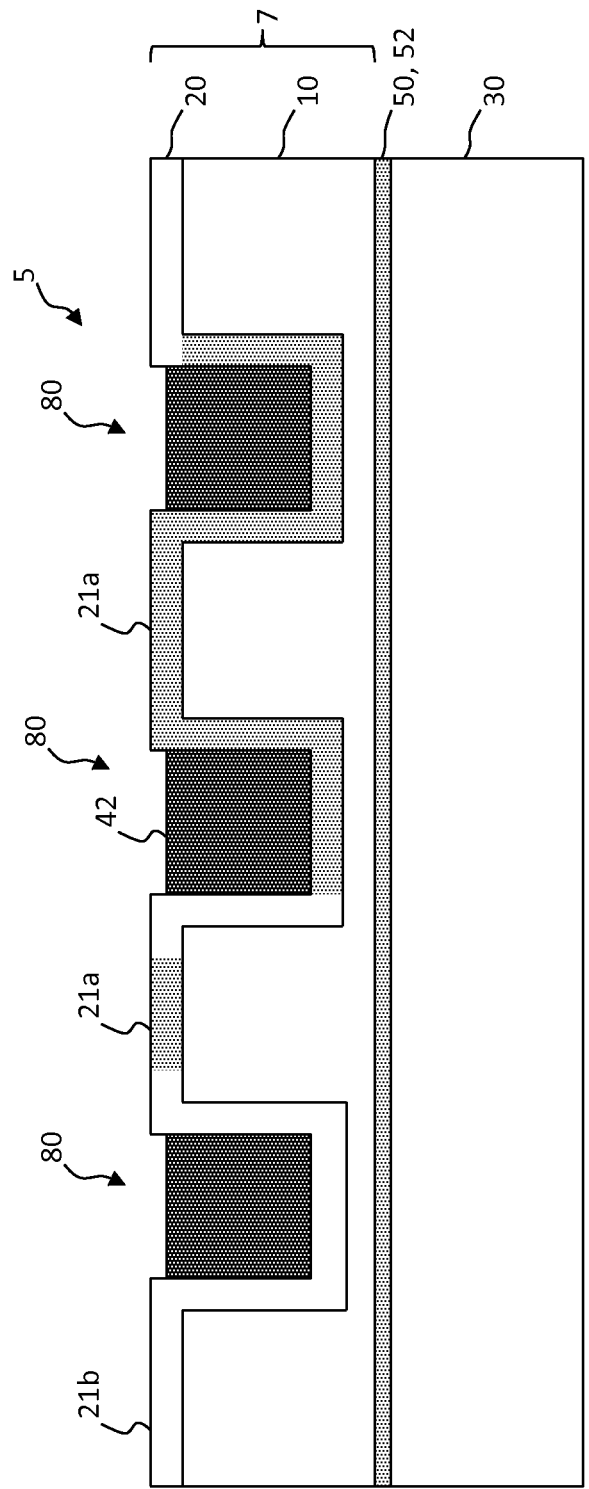

In a useful arrangement illustrated in FIG. 2B, the indentations 80 of the bi-layer 7 contain a third cured material 42, for example electrically conductive material that forms an electrical conductor. In an embodiment, such an electrically conductive third cured material 42 is formed by coating a liquid conductive ink, for example containing metallic nano-particles, over the surface of the structured bi-layer 7, removing the conductive ink from surface portions of the structured bi-layer 7 leaving remaining conductive ink in the indentations 80, and curing the liquid conductive ink to form electrical conductors. Suitable liquid conductive inks are known in the art and are electrically conductive after curing. In another embodiment, the conductivity of the third cured material 42 is greater than the conductivity of the second cured layer 20 or the patterned second cured layer 21.

A combination of the electrically conductive third cured material 42 and the patterned second cured layer 21 with conductive portions 21a and non-conductive portions 21b can form an electrical circuit or patterned conductor. The electrical circuit can electrically connect separated electrical conductors in the indentations 80 or can include separate circuits in the indentations 80 and the patterned second cured layer 21. The electrical circuit can connect electronic computing devices such as integrated circuits (not shown).

Figure 3:
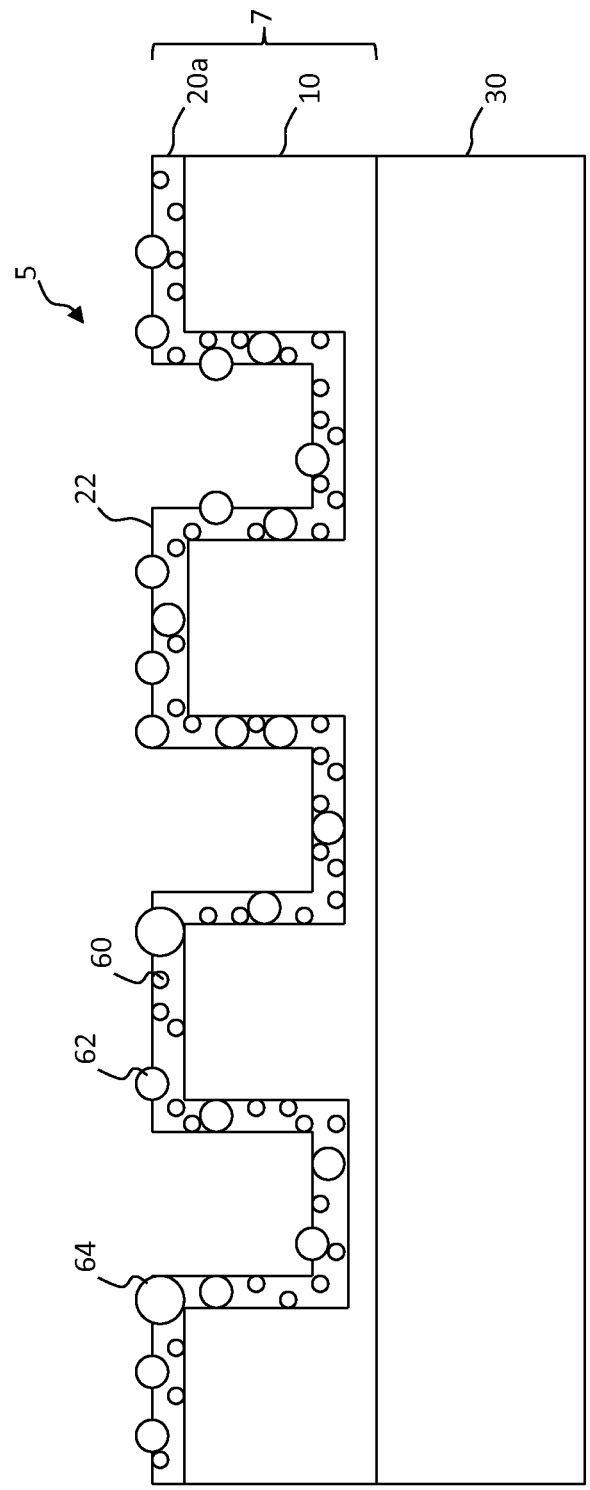
FIG. 3 is a cross section of a multi-layer structure including particles in an embodiment of the present invention.

Referring to FIG. 3 in another useful embodiment of the imprinted multi-layer structure 5 having the bi-layer 7, the second cured layer 20 (FIG. 1) includes particles 60 that can be biocidal particles 60, for example that have a silver component, have a sulfur component, have a copper component, are a salt, are a silver sulfate salt or other biocidal particles, or include phosphors to form a biocidal second cured layer 20a. In an embodiment, the biocidal second cured layer 20a has a surface 22 on a side of the biocidal second cured layer 20a opposite the first cured layer 10 and support 30 and portions of the particles 60 extend beyond the surface 22 forming exposed particles 62. The particles 60 can also have a distribution of sizes so that some of the particles 60 are large particles 64 that can, but do not necessarily, extend beyond the surface 22 and are therefore also exposed particles 62. The particles 60 are located within and between the indentations 80 of the structure bi-layer 7 and include both the large particles 64 and the exposed particles 62.

In this embodiment, the second cured layer 20 (FIG. 1) is a biocidal second cured layer 20a. By biocidal layer is meant herein any layer that resists the growth of undesirable biological organisms, including microbes, bacteria, or fungi or more generally, eukaryotes, prokaryotes, or viruses. In particular, the biocidal second cured layer 20a inhibits the growth, reproduction, or life of infectious micro-organisms that cause illness or death in humans or animals and especially antibiotic-resistant strains of bacteria. The biocidal second cured layer 20a is rendered biocidal by including particles 60 such as ionic metals or metal salts in the biocidal second cured layer 20a. The particles 60 reside in the biocidal second cured layer 20a. In an embodiment, some of the particles 60 in the biocidal second cured layer 20a are exposed particles 62 that extend from the second-layer first side 22 into the environment and can interact with any environmental contaminants or biological organisms in the environment. Exposed particles 62 are thus more likely to be efficacious in destroying microbes. In various embodiments, the particles 60 are silver or copper, are a metal sulfate, have a silver component, are a salt, have a sulfur component, have a copper component, are a silver sulfate salt, or include phosphors. In an embodiment, the biocidal second cured layer 20a is thinner than the first cured layer 10 so that the second-layer thickness 26 is less than the first-layer thickness 16, thus reducing the quantity of particles 60 that are required in the biocidal second cured layer 20a. In an alternative embodiment, the second-layer thickness 26 is greater than the first-layer thickness 16.

In an embodiment, the particles 60 are coated, for example with the material in the second cured layer 20 (FIG. 1).

In other embodiments, the biocidal second cured layer 20a has a thickness that is less than at least one diameter of one or more of the particles 60, has a thickness that is less than a mean diameter of the particles 60, or has a thickness that is less than the median diameter of the particles 60. Alternatively, the particles 60 have at least one diameter between 0.05 and 25 microns. In such embodiments, one or more of the particles 60 will be exposed particles 62. If such exposed particles 62 are biocidal, the exposed particles 62 can inhibit the growth or reproduction of microbes or destroy any microbes on the surface of the biocidal second cured layer 20a. In yet another arrangement, the biocidal second cured layer 20a is greater than or equal to 0.5 microns thick and less than or equal to 20 microns thick or the first cured layer 10 on the support 30 includes particles 60 (not shown in FIG. 3).

The indentations 80 form a topographical non-planar layer in the second cured layer 20, the patterned second cured layer 21, or the biocidal second cured layer 20a that is not smooth and is inhospitable to the growth and reproduction of microbes. In yet another embodiment, the first or second cured layers 10, 20, the patterned second cured layer 21, or the biocidal second cured layer 20a have a hydrophobic surface, for example by providing a roughened surface either by imprinting or by a treatment such as sandblasting or exposure to energetic gases or plasmas.

Referring to FIGS. 4A to 4F and FIG. 7, a method of the present invention includes making the imprinted multi-layer structure 5 having the support 30 (FIG. 4A) in step 100 (FIG. 7). A first curable layer 13 including a first material is located on or over the support 30 (FIG. 4B) in step 105. A second curable layer 23 including a second material different from the first material is located on or over the first curable layer 13 in step 110 (FIG. 4C) before the first curable layer 13 is cured. The first curable layer 13 and the second curable layer 23 are formed in various ways, including extrusion or coating, for example spin coating, curtain coating, or hopper coating, or other methods known in the art. In other embodiments of the present invention, locating the first curable layer 13 includes laminating a first curable material on or over the support 30 or locating the second curable layer 23 includes laminating a second curable material on or over the first curable layer 13.

Figure 4A:
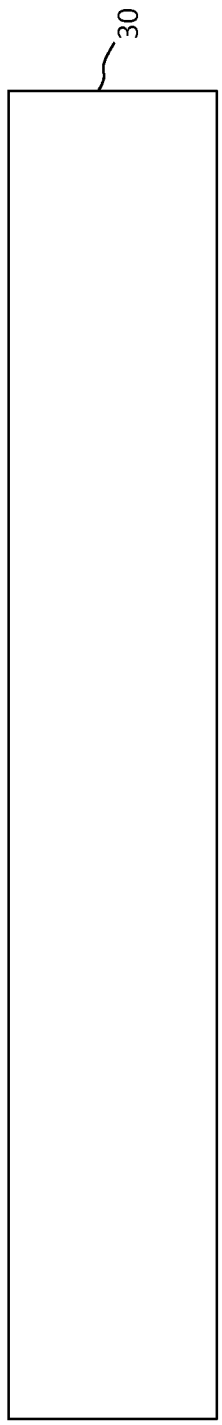
Figure 4B:
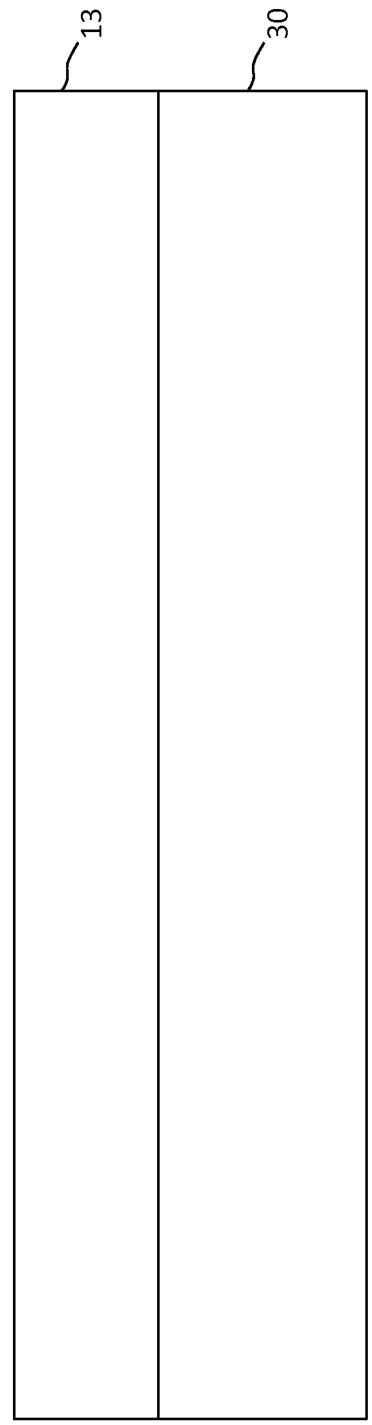
Figure 4C:
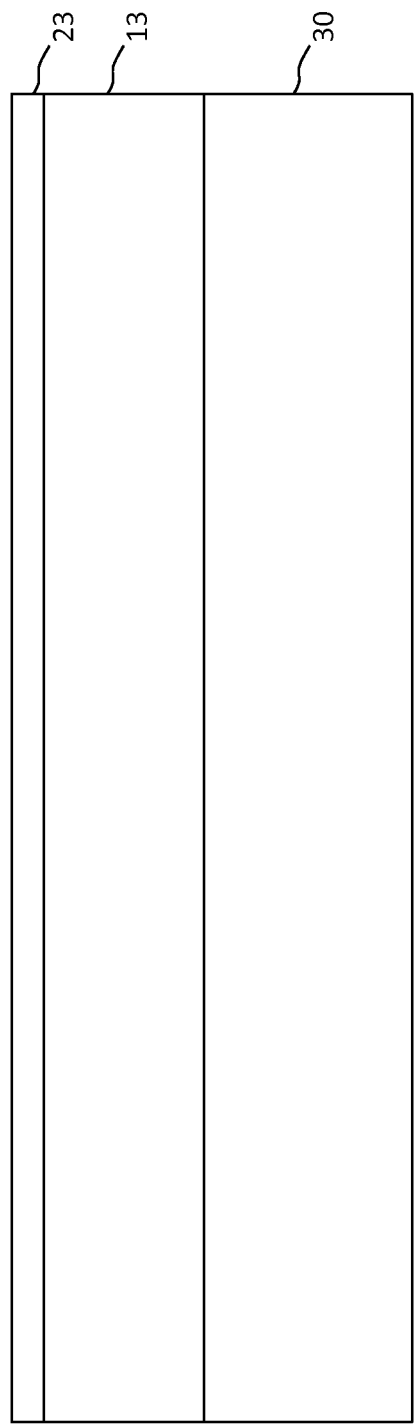
Figure 4D:
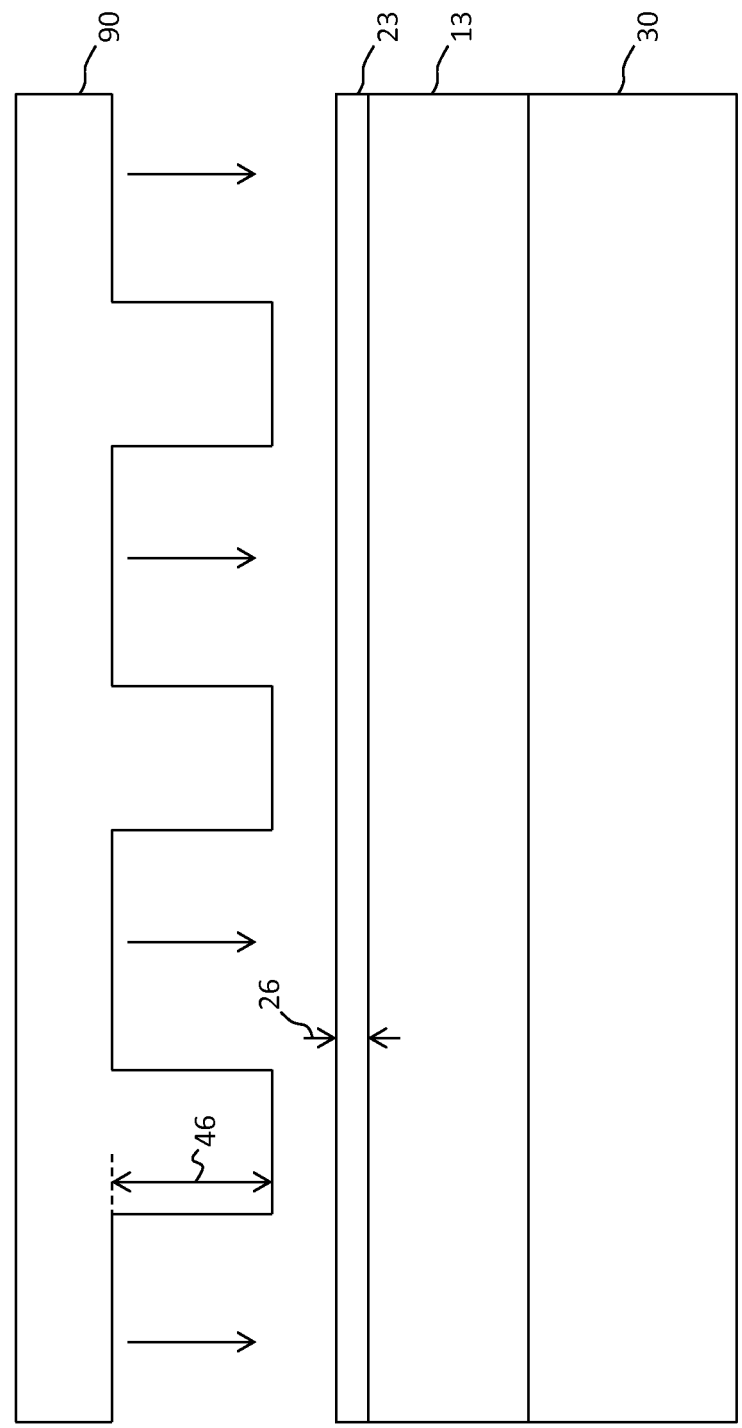
Figure 4E:
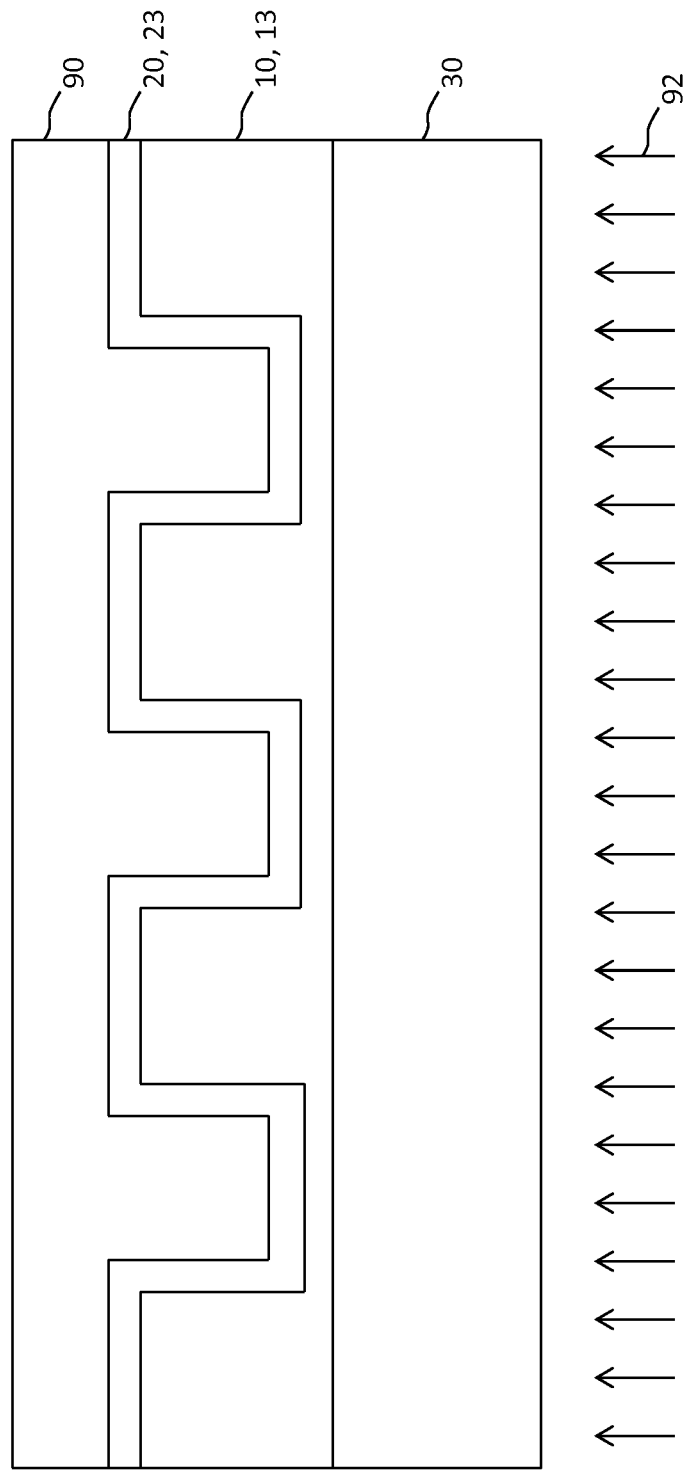

The first curable layer 13 and the second curable layer 23 are imprinted in a single step 125 with an imprinting stamp 90 having a structure with a structure depth 46 greater than the second layer thickness 26 of the second curable layer 23 (FIG. 4D) and then cured in a single step 130, for example with heat or radiation 92 to form the first cured layer 10 and the second cured layer 20 (FIG. 4E). The imprinting stamp 90 is removed in step 135 to form an imprinted structured bi-layer 7 with a structure depth 46 greater than the second-layer thickness 26 of the second cured layer 20 (FIG. 4F) to form the structured bi-layer 7 of the imprinted multi-layer structure 5 of the present invention.

An imprinted multi-layer structure 5 having the structured bi-layer 7 of the present invention has been constructed in a method of the present invention using cross-linkable materials such as curable resins (for example using SU8 at suitable viscosities and PEDOT) coated on a glass surface and imprinted using a PDMS stamp to form micro-structures in the bi-layer 7. Electrically conductive PEDOT layers have been patterned to form circuit or wiring patterns and conductive inks have been located and cured in the micro-channels to form cured conductive wires.

Referring further to FIG. 7 in an embodiment of the present invention, the surface 8 of the structure 40 is identified in step 150. The surface 8 is a surface which it is desired to keep free of microbes, for example a wall, floor, table top, door, handle, knob, cover, or device surface, especially any surface 8 found in any type of medical institution. In an embodiment, the surface 8 is planar; in another embodiment, the surface 8 is non-planar. In step 155, an adhesive is located, for example on the surface 8 or on the side of the support 30 opposite the first cured layer 10, to form the adhesive layer 50. The support 30 is adhered to the surface 8 in step 160. In a further embodiment, the support 30, first cured layer 10, and second cured layer 20 are heated to shrink the imprinted multi-layer structure 5 on the surface 8 if the surface 8 is non-planar. In an embodiment, the heating step (not shown separately) is also the adhesion step 160 and a separate adhesive layer 50 is not necessary or used. In an embodiment, the second cured layer 20 is thinner than the first cured layer 10.

In another embodiment, referring to FIG. 2, the third cured material 42, for example a liquid conductive ink, is located in the indentations 80 of the bi-layer 7, for example by coating the surface and indentations 80 of the second cured layer 20 with a liquid conductive ink, wiping the surface of the second cured layer 20 to remove excess liquid conductive ink from the surface but not the indentations 80, and curing the liquid conductive ink in the indentations 80 to form an electrical conductors in each of the indentations 80. Such coating, wiping, and curing methods and materials are known in the art.

Figure 5A:
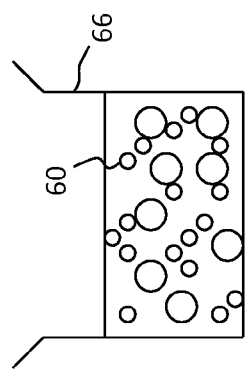
FIGS. 5A-5F are cross sections of sequential construction steps useful in another method of the present invention.

Referring next to FIGS. 5A to 5F and to FIG. 7 again, a dispersion of particles 60 is formed in step 120 in the second cross-linkable material for example before locating a biocidal second curable layer 23a on or over the first curable layer 13 (FIG. 5A). In an embodiment, a dispersion of particles 60 is formed in a carrier such as a liquid, for example a curable resin, in a container 66. Making and coating liquids with dispersed particles is known in the art. A dispersion having antimicrobial particles 60 has been made. The dispersion included three-micron silver sulfate particles milled in an SU8 liquid to an average particle size of one micron, and successfully coated on glass and tested with *E. coli* bacteria. In an alternative, the biocidal second curable layer 23a is made separately and laminated on or over the first curable layer 13.

Figure 5B:
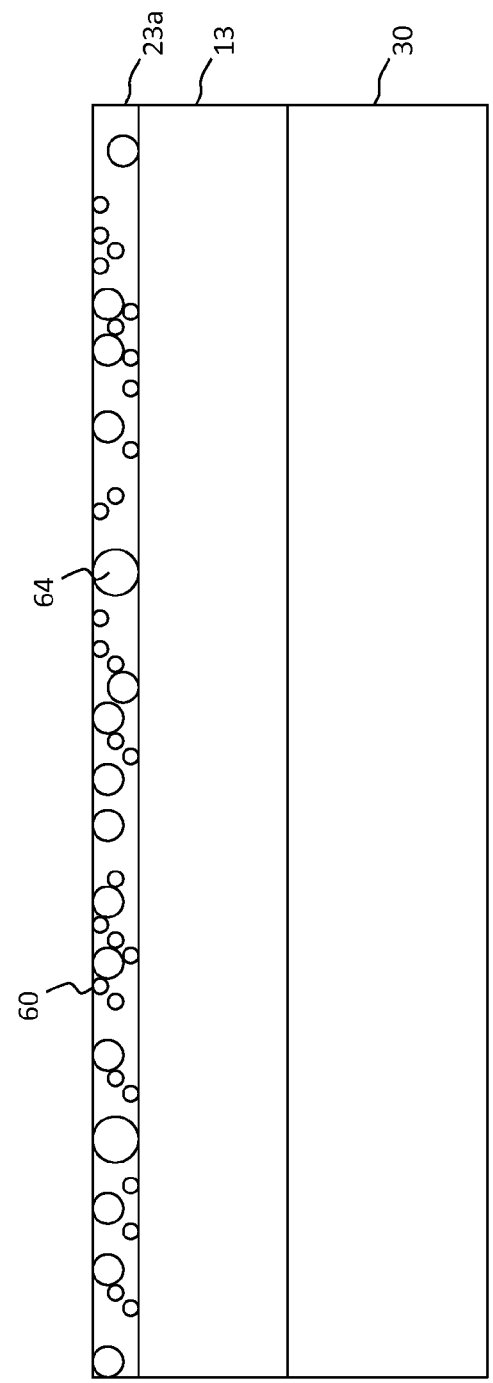
Figure 5C:
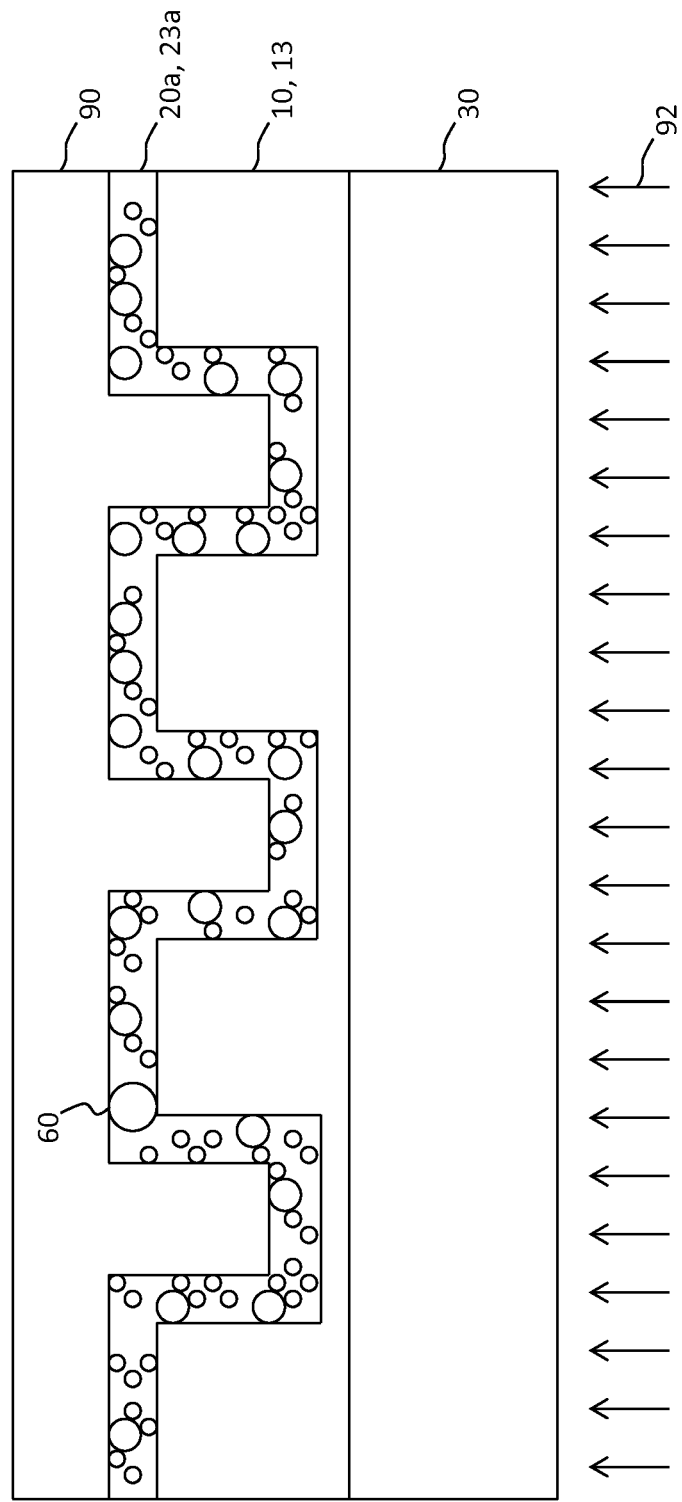
Figure 5D:
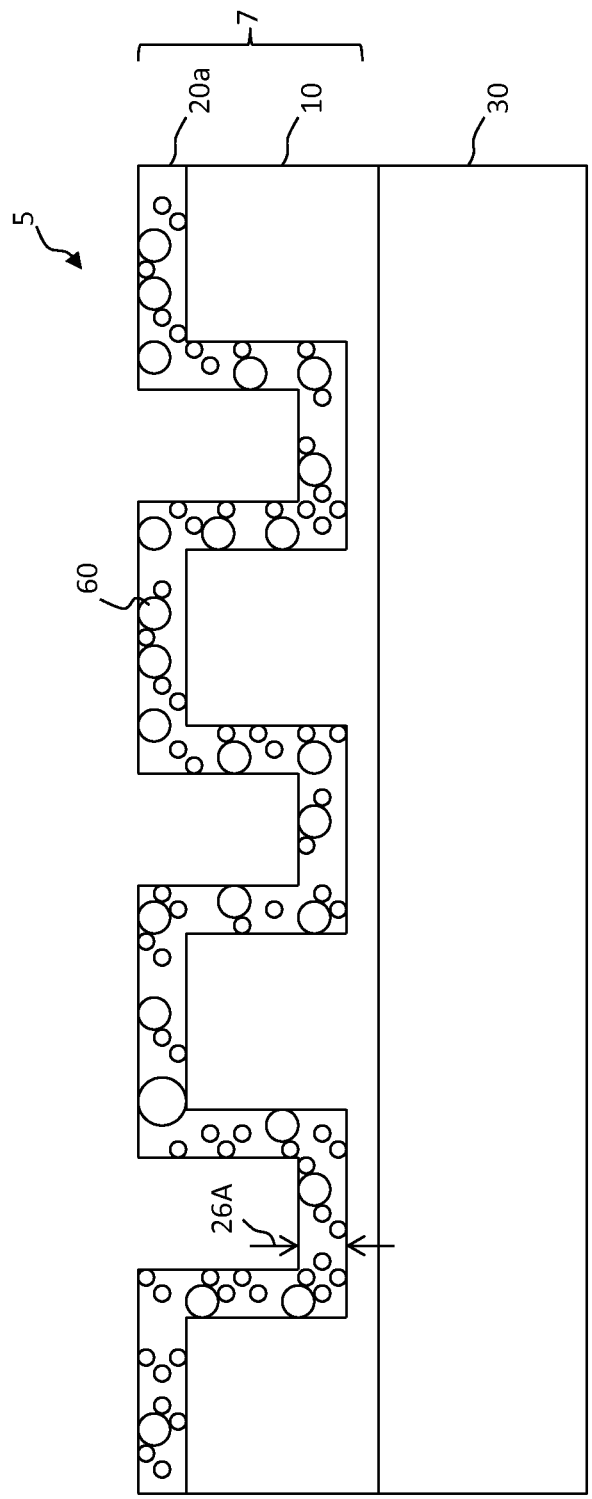

After steps 100 and 105 of FIG. 7 and as shown in FIGS. 4A and 4B, the dispersion is coated or a layer laminated on the first curable layer 13 to form the biocidal second curable layer 23a (FIG. 5B). The silver sulfate particle dispersion noted above was spin-coated on the glass support 30, cured, and tested for anti-microbial efficacy. As shown in FIG. 5C, the first curable layer 13 and biocidal second curable layer 23a (the biocidal second curable layer 23a including the particles 60) on the support 30 are imprinted in step 125 with the stamp 90 and cured with radiation 92 in step 130 to form the first cured layer 10 and biocidal second cured layer 20a. In an embodiment, the curing step 130 includes cross-linking the first curable layer 13 to the biocidal second curable layer 23a. The stamp is removed in step 135 to form the imprinted multi-layer structure 5 having the structured bi-layer 7 shown in FIG. 5D. Imprinting methods using stamps are known in the art.

Figure 5E:
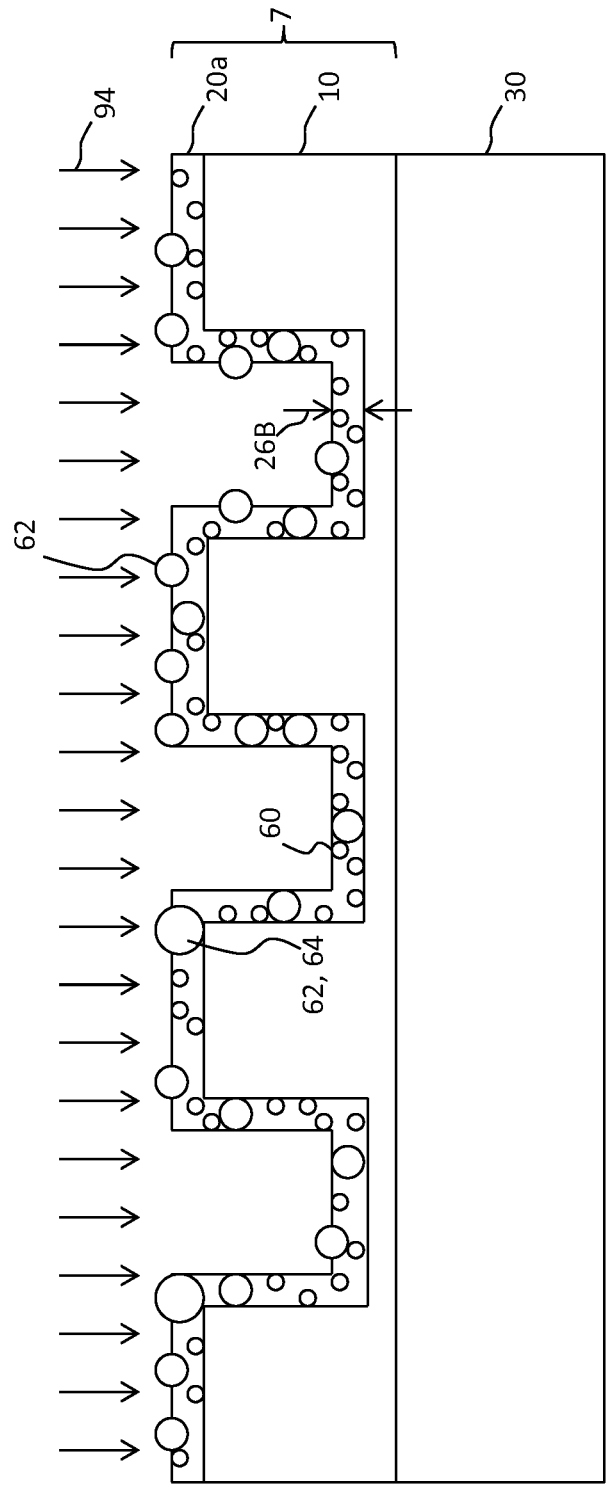

As shown in FIG. 5E, in a further embodiment of the present invention, a portion of the biocidal second cured layer 20a is removed in step 140, for example by etching or using energetic particles 94 such as with plasma etching, reactive plasma etching, ion etching, or sandblasting the first cured layer 10 or the biocidal second cured layer 20a. Such a removal treatment can remove any coating over the exposed particles 62 and further expose the exposed particles 62 to the environment. Alternatively, particles 60 are exposed by washing the first or second cured layer 10, 20. In an embodiment, the second-layer thickness 26B after the removal step 140 is less than the second-layer thickness 26A (FIG. 5D) before the removal step 140.

Figure 5F:
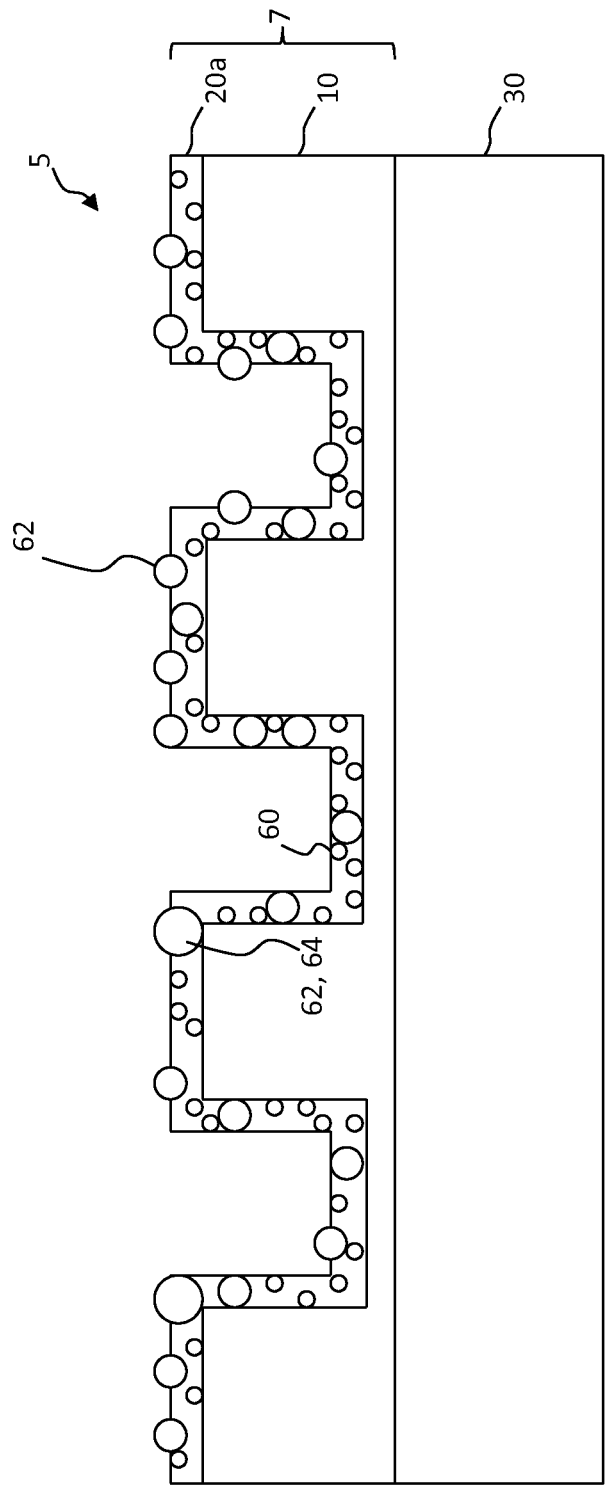

As shown in FIG. 5F, the result of the process is an imprinted multi-layer structure 5 with a structured bi-layer 7 including first cured layer 10 and biocidal second cured layers 20a on the support 30. The biocidal second cured layer 20a includes particles 60, including large particles 64 and exposed particles 62 in a second material, for example a second cured material. A coating of silver sulfate particles dispersed in SU8 has been exposed to plasma to reduce the coating thickness and further expose the particles 60 to the environment.

In an embodiment, the first cured layer 10 includes a first cross-linkable material, the biocidal second cured layer 20a includes a second cross-linkable material and the curing step 130 cross-links the first cross-linkable material to the second cross-linkable material. In another embodiment, the first material includes a first cross-linkable material and the second material includes a second cross-linkable material that is different from the first cross-linkable material and the curing step 130 cross-links the first cross-linkable material to the second cross-linkable material. Alternatively, the first material includes a first cross-linkable material, the second material includes a second cross-linkable material that is the same as the first cross-linkable material, and a third material is included in either the first material or the second material but not both the first and second materials and the curing step 130 cross-links the first cross-linkable material to the second cross-linkable material.

In another embodiment of the present invention, referring back to FIG. 1, the first cured layer 10 and the second cured layer 20 are not necessarily cross-linked. In such an embodiment, the biocidal imprinted multi-layer structure 5 includes the support 30 and the bi-layer 7 having a topographical structure on or over the support 30. The structured bi-layer 7 includes the first cured layer 10 on or over the support 30 and the second cured layer 20 on or over the first cured layer 10 on a side of the first cured layer 10 opposite the support 30. The structure of the structured bi-layer 7 has at least one structure depth 46 that is greater than the second-layer thickness 26 of the second cured layer 20. In an embodiment, multiple biocidal particles 60 are located only in the second cured layer 20.

Similarly, according to a method of the present invention and referring again to FIG. 7 and FIGS. 5A-5F, a method of making a biocidal imprinted multi-layer structure 5 includes providing the support 30 in step 100, locating the first curable layer 13 on the support 30 in step 105, forming a dispersion of multiple biocidal particles 60 in step 120, locating the biocidal second curable layer 23a on the first curable layer 13 in step 110 using the dispersion, the biocidal second curable layer 23a having multiple biocidal particles 60 dispersed within the biocidal second curable layer 23a, imprinting the first curable layer 13 and the biocidal second curable layer 23a in a single step with an imprinting stamp 90 having a structure with a depth greater than the thickness of the biocidal second curable layer 23a in step 125, curing the first curable layer 13 and the biocidal second curable layer 23a in a single step to form the first cured layer 10 and the biocidal second cured layer 20a in step 130, and removing the imprinting stamp 90 in step 135.

In yet another embodiment of the present invention, not separately illustrated, the layer on a side of the first cured layer 10 opposite the support 30 (e.g. corresponding to the second cured layer 20) is a second layer that is not necessarily a cured layer and is not cross-linked. In various embodiments, this second layer is non-conductive, conductive, pattern-wise conductive, or include biocidal particles 60. The second layer is in a spatial relationship to the first cured layer 10 on a side of the first cured layer 10 opposite the support 30. The structure of the structured bi-layer 7 has at least one structure depth 46 that is greater than the second-layer thickness 26 of the second layer. Multiple biocidal particles 60 are located only in the second layer. In an embodiment the particles 60 are fixed in, fixed on, or adhered to the cross-linked material in the first cured layer 10.

Figure 6A:
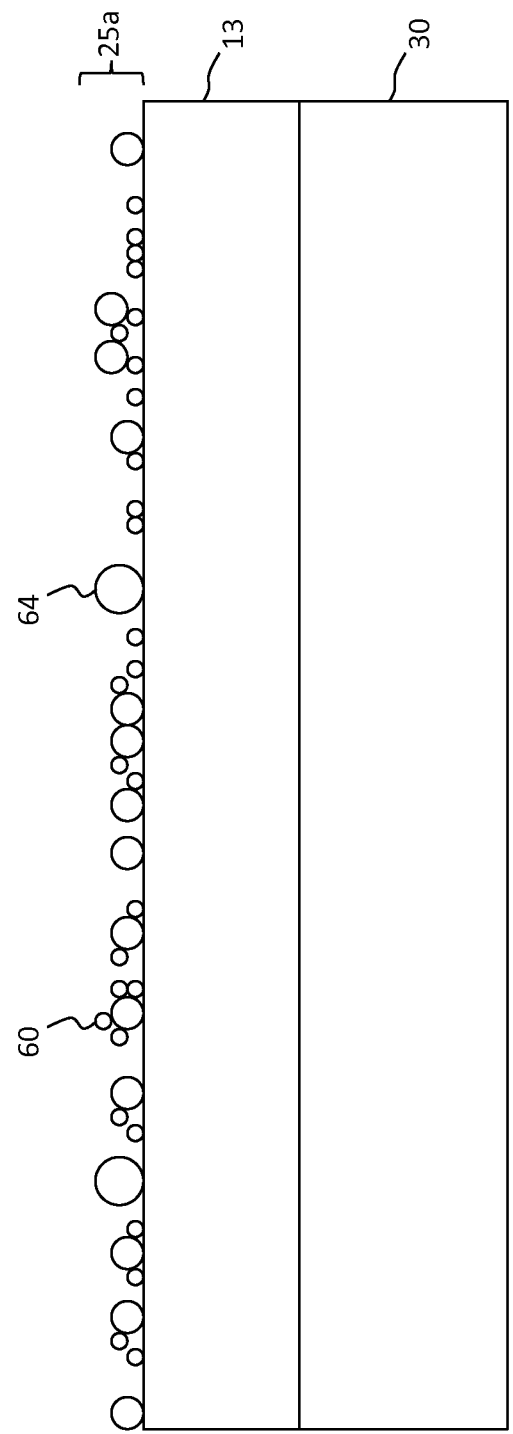
FIGS. 6A-6D are cross sections of sequential construction steps useful in yet another method of the present invention.
Figure 8B:
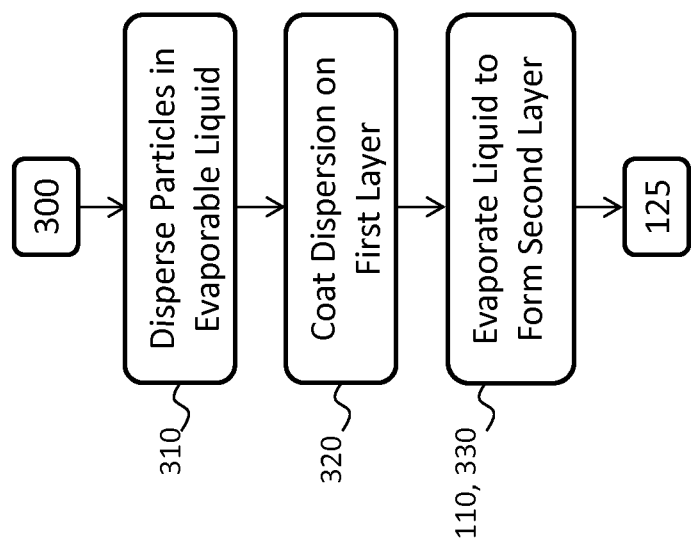
FIGS. 8A and 8B are flow diagrams illustrating alternative methods of the present invention.
Figure 8A:
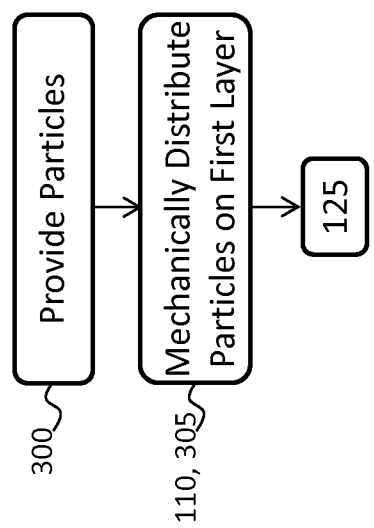

Referring to the sequential structures illustrated in FIGS. 6A-6D and the flow charts of FIGS. 8A and 8B, an alternative method of making a biocidal bi-layer 7 includes providing the support 30 in step 100 and locating the first curable layer 13 on the support 30 in step 105 (as shown in FIG. 7). Referring to FIG. 8A and FIG. 6A, a biocidal second layer 25a is located on or over the first curable layer 13. The biocidal second layer 25a includes multiple biocidal particles 60 located within the second cured layer 20.

Referring specifically to FIG. 8A in an embodiment, the biocidal particles 60 are provided in step 300 and then mechanically distributed over the first curable layer 13 in step 305. For example, the particles are agitated within a container or on a surface to form a uniform distribution of particles 60 and then released above the first curable layer 13 so that the particles 60 fall under the influence of gravity onto the first curable layer 13. Ways to distribute particles 60 over a layer are known in the art. The distribution of particles 60 on the first curable layer 13 forms the biocidal second layer 25a on the first curable layer 13 (equivalent to step 110 in FIG. 7) as shown in FIG. 6A.

Referring specifically to FIG. 8B, in an alternative embodiment, particles 60 are provided in step 300 and dispersed into an evaporable liquid in step 310 (and as shown in step 120 in FIG. 7) to form a dispersion. This dispersion is distinguished from that of FIG. 5A in that is evaporable rather than curable. The dispersion is coated on or over the first curable layer 13 in step 320, for example by spin coating, hopper coating, curtain coating or other methods known in the art. The dispersion is then dried in step 330 (and as shown in step 110 of FIG. 7), for example by heating or drying without curing the first curable layer 13 or at least without completely curing the first curable layer 13, to form the biocidal second layer 25a. The biocidal second layer 25a is formed as a layer of particles 60 on the surface of the first curable layer 13 as shown in FIG. 6A.

Figure 6B:
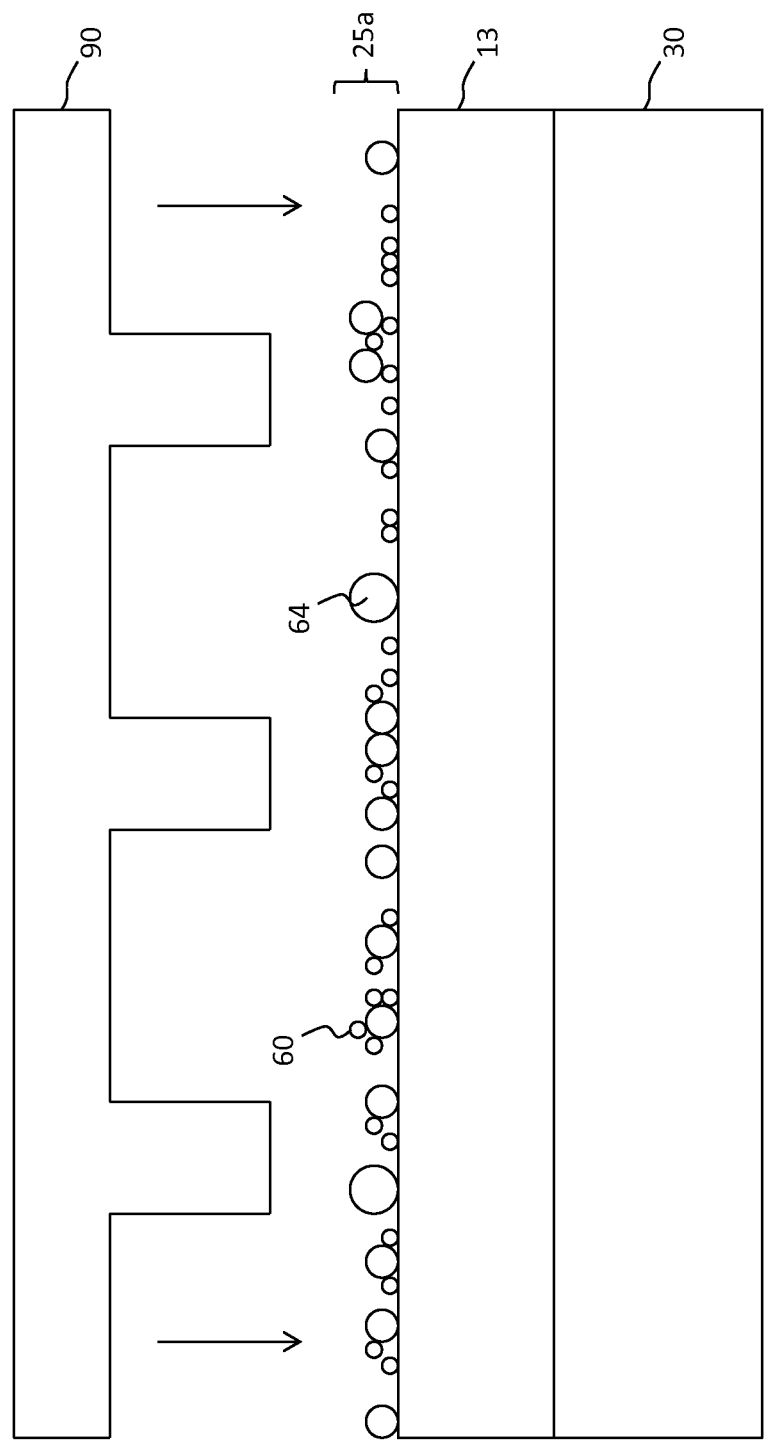
Figure 6C:
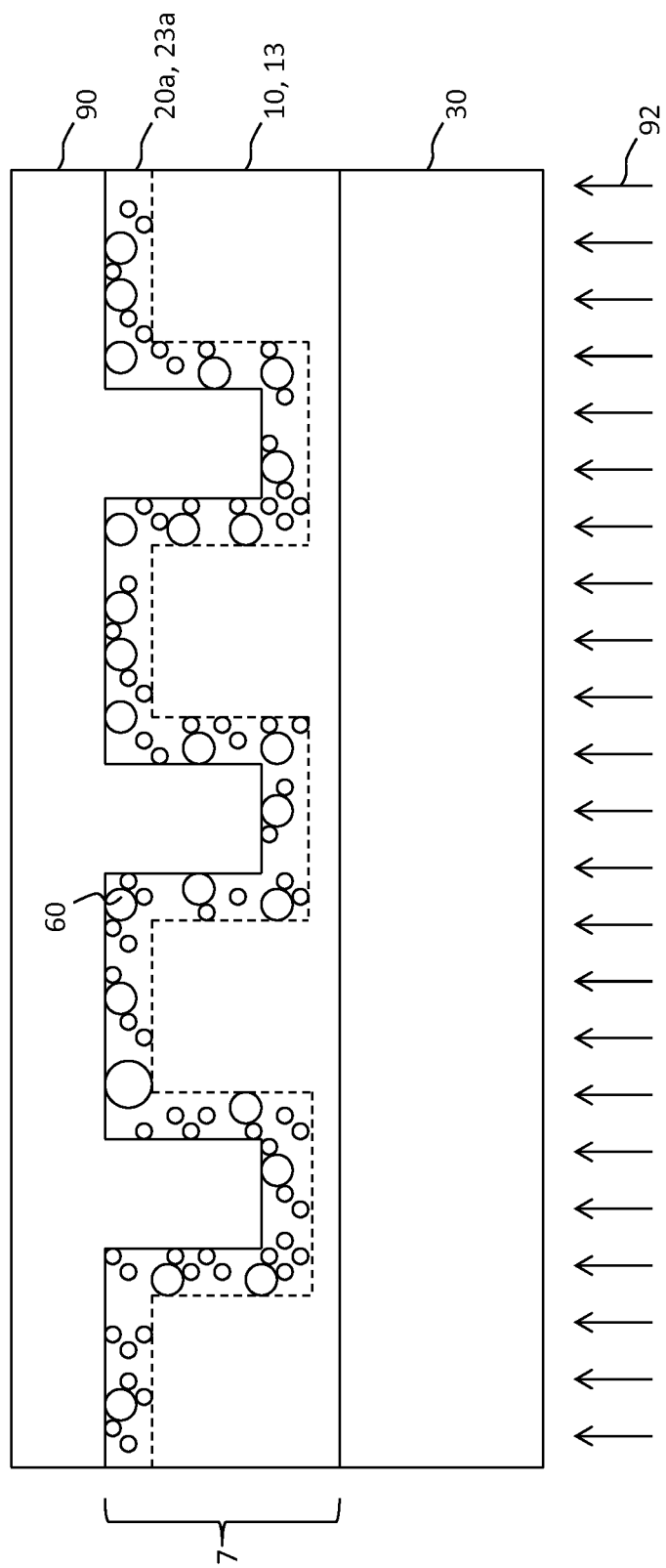
Figure 6D:
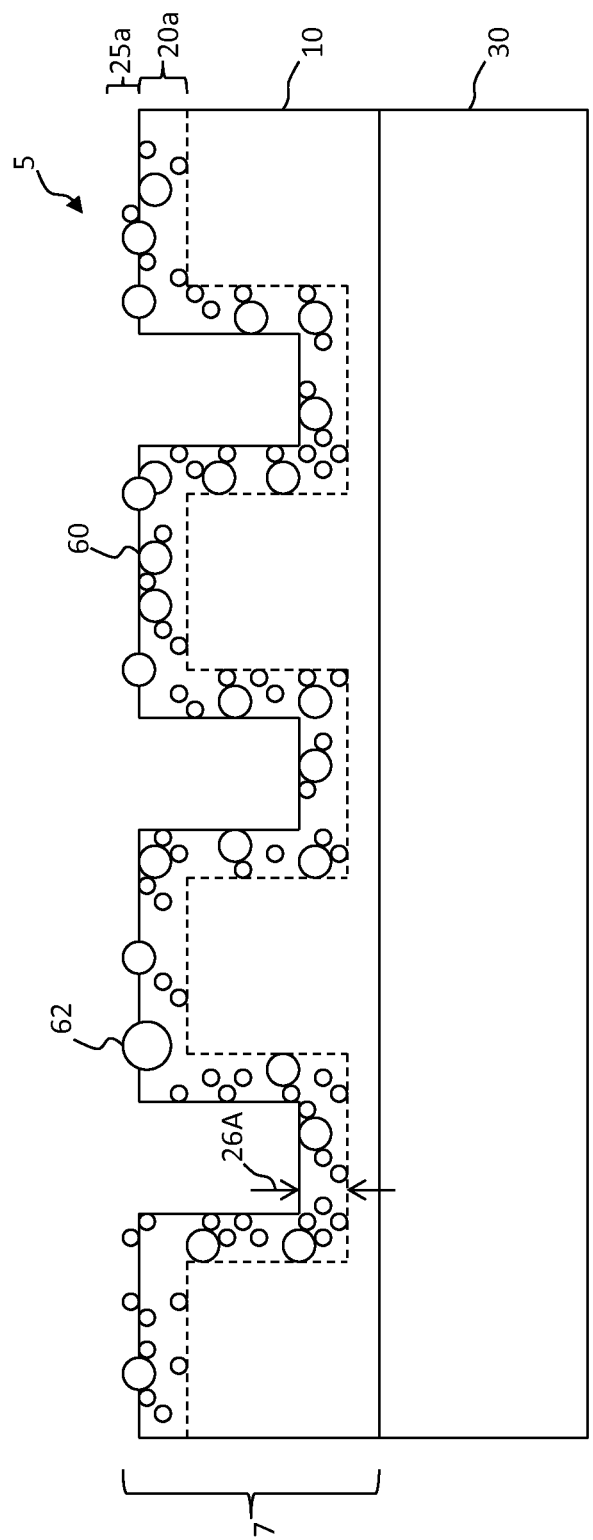

The first curable layer 13 and the biocidal second layer 25a are then imprinted with an imprinting stamp having a structure with a depth greater than the thickness of the second curable layer in a single step in step 125, referring now to FIG. 7 and as shown in FIG. 6B. As shown in FIG. 6C, the particles 60 of the biocidal second layer 25a are impressed by the imprinting stamp into the first curable layer 13. In one embodiment of the present invention, the particles 60 of the biocidal second layer 25a are impressed completely into the first curable layer 13 so that the biocidal second layer 25a is a part of the first curable layer 13 (as shown in FIG. 6C) and is transformed into the biocidal second curable layer 23a. In this case, the biocidal second curable layer 23a overlaps with the first curable layer 13 so that the entire biocidal second curable layer 23a is in common with a portion of the first curable layer 13. In an alternative embodiment of the present invention shown in FIG. 6D, at least some of the particles 60 of the biocidal second layer 25a (FIG. 6B) are impressed only part way into the first curable layer 13 so that the biocidal second curable layer 23a overlaps a part of the first curable layer 13. The exposed particles 62 extending beyond the surface of the first curable layer 13 (as shown in FIG. 6D) form the biocidal second layer 25a and does not overlap with the first curable layer 13.

In step 130, the first curable layer 13 and the second curable layer 23 (or biocidal second curable layer 23a) is cured in a single step to form the first cured layer 10 and second cured layer 20 or biocidal second cured layer 20a and fix the particles 60 in the bi-layer 7. If the first curable layer 13 includes a cross-linkable material, the step 130 of curing the first curable layer 13 and the second curable layer 23 or biocidal second curable layer 23a fixes the particles 60 within the cross-linkable material. In step 135, the imprinting stamp is removed. Optionally, a portion of the second layer is removed in step 140 and the bi-layer 7 adhered to the surface 8.

In the embodiments of FIGS. 8A and 8B, the biocidal second curable layer 23a with the particles 60 is considered to overlap with the first curable layer 13 and the first cured layer 10 so that a portion of the first curable layer 13 is in common with the second curable layer 23 or biocidal second curable layer 23a. In an alternative understanding, a portion of the first curable layer 13 is converted into the second curable layer 23 or biocidal second curable layer 23a when the particles 60 are impressed into the first curable layer 13 so that the first curable layer 13 is reduced in thickness and at least a portion of the second curable layer 23 or biocidal second curable layer 23a is cured. These understandings of the first curable layer 13 and second layer (second curable layer 23, biocidal second curable layer 23a, or biocidal second layer 25a) and understanding of the first cured layer 10 and second layer (second cured layer 20, biocidal second cured layer 20a, biocidal second layer 25a) are equivalent in practice, since they result in a layer of particles at least partially embedded in the first cured layer 10. Essentially, the second curable layer 23, biocidal second curable layer 23a, and biocidal second layer 25a are all embodiments of a second layer formed on first curable layer 13 before the first curable layer 13 is cured to form the first cured layer 10. Likewise, the second cured layer 20, biocidal second cured layer 20a, and biocidal second layer 25a are all embodiments of a second layer formed on first cured layer 10 after the first curable layer 13 is cured to form the first cured layer 10. To illustrate these different understandings of the first cured layer 10 and the biocidal second cured layer 20a or biocidal second layer 25a, a dashed line demarcates the two layers in FIGS. 6C and 6D. Whether the layers are considered to be separate layers or to overlap is a matter of perspective having little practical consequence.

Thus, in various embodiments, a portion of a second layer is in common with a portion of the first cured layer 10 or an entire second layer is in common with a portion of the first cured layer 10. In various embodiments, the second layer is a curable or cured layer, is non-conductive, is conductive, or includes biocidal particles. In yet another embodiment, cured portions of the second layer are removed (step 140) so that only the particles 60 remain adhered to the first cured layer 10 so that none of the second layer is in common with a portion of the first cured layer 10 (not shown).

In yet another embodiment, the first cured layer 10 or the second cured layer 20, biocidal second cured layer 20a, or biocidal second layer 25a have a hydrophobic surface, for example by providing a roughened surface either by imprinting or by a treatment such as sandblasting or exposure to energetic gases or plasmas or from the presence of the biocidal particles 60.

In a further embodiment of the present invention, the first cured layer 10, the second cured layer 20, the biocidal second cured layer 20a, or the support 30 is or includes a heat-shrink film, for example polyolefin, polyvinylchloride, polyethylene, or polypropylene. Any of the first cured layer 10, the second cured layer 20, the biocidal second cured layer 20a, or the support 30 can include cross linking materials that are cross linked for example by radiation or heat to provide strength.

Figure 9:
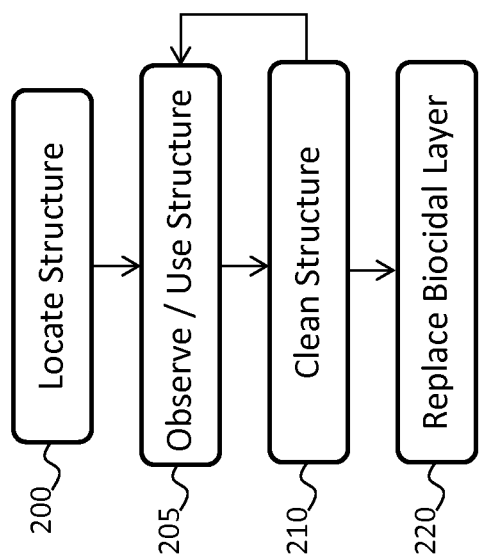
FIG. 9 is a flow diagram illustrating another method of the present invention.

Referring to FIG. 9, in various embodiment of the present invention, any of the biocidal bi-layers 7 or the biocidal imprinted multi-layer structures 5 described above, including those of FIG. 3, 5D, 5F, or 6D is located on a surface 8 in step 200 and observed over time in step 205. Periodically or as needed, the imprinted multi-layer structure 5 is cleaned in step 210, for example by washing with water or with a cleaning fluid, or wiping the multi-layer structure 5. The imprinted multi-layer structure 5 is repeatedly observed (step 205) and cleaned (step 210) until it is no longer efficacious for its intended purpose. The biocidal imprinted multi-layer structure 5 is replaced, removed, or covered over in step 220.

In an embodiment, the cleaning step removes dead micro-organisms or dirt from the surface 22 of the biocidal second cured layer 20a so that the biocidal efficacy of the particles 60 is improved in the absence of the dead micro-organisms or dirt. Useful cleaners include hydrogen peroxide, for example 2% hydrogen peroxide, water, soap in water, or a citrus-based cleaner. In an embodiment, the 2% hydrogen peroxide solution is reactive to make oxygen radicals that improve the efficacy of particles 60. In various embodiments, cleaning is accomplished by spraying the surface 22 of the biocidal second cured layer 20a with a cleaner and then wiping or rubbing the surface 22. The cleaner can dissolve the biocidal second cured layer 20a material (e.g. cross linking material) and the wiping or rubbing can remove dissolved material or abrade the surface 22 of the biocidal second cured layer 20a to expose other particles 60 or increase the exposed surface area of exposed particles 62.

Alternatively, the cleaning or washing step 210 refreshes the particles 60, for example by a chemical process, to improve their biocidal efficacy. This can be done, for example, by ionizing the particles 60, by removing oxidation layers on the particles 60, or by removing extraneous materials such as dust from the particles 60.

Replacement of the biocidal second cured layer 20a or biocidal second layer 25a can proceed in a variety of ways. In one embodiment, another biocidal imprinted multi-layer structure 5 is simply located over the biocidal imprinted multi-layer structure 5. Thus, the biocidal multi-layer structure 5 becomes the structure 40 and another biocidal imprinted multi-layer structure 5 is applied to the structure 40, for example with an adhesive layer 50 (FIG. 1). In another embodiment, the biocidal imprinted multi-layer structure 5 is removed and another biocidal imprinted multi-layer structure 5 put in its place. As shown in FIG. 1, the support 30 is adhered to the structure 40 with an adhesive layer 50. Chemical or heat treatments are applied to the biocidal multi-layer structure 5 to loosen, dissolve, or remove the adhesive layer 50 so the biocidal imprinted multi-layer structure 5 can be removed and another adhesive layer 50 applied to the structure 40 to adhere the biocidal imprinted multi-layer structure 5 to the structure 40. In an embodiment, the biocidal imprinted multi-layer structure 5 is peeled from the structure 40 and another biocidal imprinted multi-layer structure 5 having an adhesive layer 50 is adhered to the structure 40.

Alternatively, portions of the biocidal imprinted multi-layer structure 5 are removed, for example at least a portion of the biocidal second cured layer 20a is mechanically separated from the first cured layer 10. In an embodiment, the biocidal second cured layer 20a is peeled from the first cured layer 10. Alternatively, the biocidal second cured layer 20a is abraded and removed by abrasion from the first cured layer 10. In another embodiment, the biocidal second cured layer 20a is chemically separable from the first cured layer 10 or chemically dissolvable in a substance that does not dissolve the first cured layer 10. In a useful embodiment, a substance that chemically separates the biocidal second cured layer 20a from the first cured layer 10 or that chemically dissolves the biocidal second cured layer 20a is a cleaning agent. In an embodiment, the biocidal second cured layer 20a is repeatedly cleaned, for example by spraying the biocidal second cured layer 20a with a cleaning agent and then rubbing or wiping the biocidal second cured layer 20a, and at each cleaning a portion of the biocidal second cured layer 20a is removed to gradually expose the first cured layer 10.

In another embodiment of the present invention, fluorescent or phosphorescent materials are included in the second cured layer 20 or biocidal second cured layer 20a and are illuminated. The fluorescent or phosphorescent materials respond to ultra-violet, visible, or infrared illumination and emit light that can be seen or detected and compared to a threshold emission value. Thus, the continuing presence of the second cured layer 20 or biocidal second cured layer 20a is observed. When light emission in response to illumination is no longer present at a desired level, the second cured layer 20 or biocidal second cured layer 20a is replaced.

The present invention is useful in a wide variety of environments and on a wide variety of surfaces 8, particularly surfaces 8 that are frequently handled by humans. The present invention can reduce the microbial load in an environment and is especially useful in medical facilities.

The invention has been described in detail with particular reference to certain embodiments thereof, but it will be understood that variations and modifications can be effected within the spirit and scope of the invention.

PARTS LIST 5 multi-layer structure
7 bi-layer
8 surface
10 first cured layer
13 first curable layer
16 first-layer thickness
20 second cured layer
20a biocidal second cured layer
21 patterned second cured layer
21a conductive portion
21b non-conductive portion
22 surface
23 second curable layer
23a biocidal second curable layer
25a biocidal second layer
26, 26A, 26B second-layer thickness
30 support
36 support thickness
40 structure
42 third cured material
46 structure depth
50 adhesive layer
52 binder primer
60 particle
62 exposed particle
64 large particle
66 container
80 indentations
90 stamp
92 radiation
94 energetic particles
100 provide support step
105 locate first layer step
110 locate second layer step
120 form dispersion step
125 imprint first and second layers step
130 cure first and second layers step
135 remove stamp step
140 remove second layer portion step
150 identify surface step
155 locate adhesive step
160 adhere support to surface step
200 locate structure step
205 observe structure step
210 clean structure step
220 replace biocidal layer step
300 provide particles step
305 mechanically distribute particles on first layer step
310 disperse particles in evaporable liquid step
320 coat dispersion on first layer step
330 evaporate liquid to form second layer step

The invention claimed is:

1. A method of using a multi-layer biocidal structure, comprising:
providing a multi-layer biocidal structure that includes a support and a structured bi-layer on the support, the structured bi-layer including a first cured layer on the support, an exposed second layer on and in continuous contact with the first cured layer on a side of the first cured layer opposite the support that completely covers the first cured layer, the structured bi-layer including indentations having at least one depth greater than the thickness of the second layer and multiple biocidal particles located only in the second layer; and
providing the multi-layer biocidal structure on a surface.

2. The method of claim 1, further including providing another second layer over the support.

3. A method of using a multi-layer biocidal structure, comprising:
providing a multi-layer biocidal structure that includes a support and a structured bi-layer on or over the support, the structured bi-layer including a first cured layer on or over the support, a second layer in a spatial relationship to the first cured layer on a side of the first cured layer opposite the support, the structured bi-layer having at least one depth greater than the thickness of the second layer and multiple biocidal particles located only in the second layer;

providing the multi-layer biocidal structure on a surface; and removing at least a portion of the second layer and locating another second layer over the remaining multi-layer biocidal structure.

4. The method of claim 1, further including replacing the multi-layer biocidal structure on the surface.

5. The method of claim 1, further including processing the multi-layer biocidal structure on the surface.

6. The method of claim 5, further including cleaning the multi-layer biocidal structure.

7. The method of claim 6, wherein cleaning the multi-layer biocidal structure includes abrading the second cured layer.

8. The method of claim 7, wherein abrading the second cured layer includes removing at least some particles from the second cured layer.

9. The method of claim 8, wherein abrading the second cured layer includes exposing other particles in the second cured layer.

10. The method of claim 6, wherein cleaning the multi-layer biocidal structure includes chemically processing the second cured layer.

11. The method of claim 10, wherein chemically processing the particles includes improving the biocidal efficacy of the particles.

12. The method of claim 10, wherein chemically processing the particles includes reducing the biocidal efficacy of the particles.

13. The method of claim 1, further including mechanically peeling the first and second cured layers.

14. The method of claim 1, further including chemically removing the first cured layer and second layer.

15. The method of claim 1, further including heating the first cured layer and second layer to remove them from the support.

16. The method of claim 1, further including heating the multi-layer biocidal structure to remove it from the surface.

17. The method of claim 1, further including removing a portion of the second layer to expose at least a portion of the surface of at least one of the particles.

18. A method of using a multi-layer biocidal structure, comprising:

providing a multi-layer biocidal structure that includes a support and a structured bi-layer on or over the support, the structured bi-layer including a first cured layer on or over the support, a second layer in a spatial relationship to the first cured layer on a side of the first cured layer opposite the support, the structured bi-layer having at least one depth greater than the thickness of the second layer and multiple biocidal particles located only in the second layer;

providing the multi-layer biocidal structure on a surface; and etching, plasma etching, reactive plasma etching, ion etching, or sandblasting the first cured layer or the second layer.

19. The method of claim 1, further including locating another second layer over the surface.

* * * * *